(12) United States Patent
Baloa Welzien et al.

(10) Patent No.: US 9,872,965 B2
(45) Date of Patent: Jan. 23, 2018

(54) METHOD AND SYSTEM FOR OPERATING A PATIENT VENTILATION DEVICE

(75) Inventors: Leonardo Alberto Baloa Welzien, Lake Forest, CA (US); Iva Segalman, Irvine, CA (US); Enrico Brambilla, Irvine, CA (US)

(73) Assignee: Breathe Technologies, Inc., Irvine, CA (US)

( * ) Notice: Subject to any disclaimer, the term of this patent is extended or adjusted under 35 U.S.C. 154(b) by 1322 days.

(21) Appl. No.: 13/524,983

(22) Filed: Jun. 15, 2012

(65) Prior Publication Data

US 2013/0333702 A1  Dec. 19, 2013

(51) Int. Cl.
*A61M 16/00* (2006.01)
*G06F 19/00* (2011.01)
(Continued)

(52) U.S. Cl.
CPC .... *A61M 16/0066* (2013.01); *A61M 16/0051* (2013.01); *A61M 16/0069* (2014.02);
(Continued)

(58) Field of Classification Search
CPC .... A61M 9/025; A61M 11/041; A61M 15/00; A61M 15/009; A61M 16/00;
(Continued)

(56) References Cited

U.S. PATENT DOCUMENTS 5,363,842 A * 11/1994 Mishelevich ........ A61B 8/0875
128/200.14

5,598,838 A * 2/1997 Servidio ............... A61M 16/00
128/204.21
(Continued)

FOREIGN PATENT DOCUMENTS

EP          2314333 A1      4/2011
WO   WO 2010031125 A1 *    3/2010   ........ A61M 16/0051
WO       2011056080 A1      5/2011

OTHER PUBLICATIONS

International Search Report and the Written Opinion of the International Searching (PCT/US13/39019), dated Oct. 3, 2014, 15 Pages.
(Continued)

*Primary Examiner* — Annette Dixon
(74) *Attorney, Agent, or Firm* — Stetina Brunda Garred and Brucker; Mark B. Garred (57) ABSTRACT

A patient ventilation system including a ventilation interface and a ventilation source pneumatically coupled to a patient over the ventilation interface is disclosed. There is a controller that regulates airflow delivery from the ventilation source to the patient according to one or more predefined treatment configuration settings. The controller has an inactive ventilation state, a ventilation initiation state, a treatment state, a treatment suspension state, and a ventilation deactivation state. A display interface is coupled to the controller and configured to generate, exclusively, a device activation user element with the pressure controller in the inactive ventilation state, a fitment feedback indicator and a treatment screen in a ventilation initiation state, the fitment feedback indicator and a treatment status screen in the treatment state, a treatment suspension screen in the treatment suspension state, and a treatment conclusion screen in the ventilation deactivation state.

27 Claims, 7 Drawing Sheets

(51) Int. Cl.
*A61M 16/06* (2006.01)
*A61M 16/10* (2006.01)

(52) U.S. Cl.
CPC ...... *G06F 19/3406* (2013.01); *G06F 19/3481* (2013.01); *A61M 16/06* (2013.01); *A61M 16/107* (2014.02); *A61M 2016/0027* (2013.01); *A61M 2202/0208* (2013.01); *A61M 2205/3368* (2013.01); *A61M 2205/42* (2013.01); *A61M 2205/505* (2013.01)

(58) Field of Classification Search
CPC .. A61M 2016/0021; A61M 2016/0027; A61M 2016/0039; A61M 16/01; A61M 16/06; A61M 16/08; A61M 16/1075; A61M 2016/109; A61M 16/16; A61M 16/18; A61M 2202/0208; A61M 2202/064; A61M 2205/3368; A61M 2205/42; A61M 2205/505; A61M 16/0003; A61M 16/0006; A61M 16/0009; A61M 16/0051; A61M 16/0057; A61M 16/0063; A61M 16/0066; A61M 16/0069; A61M 16/0078; A61M 16/0084; A61M 16/009; A61M 16/0093; A61M 16/021; A61M 16/024; A61M 16/026; A61M 16/04; A61M 16/0465; A61M 16/0816; A61M 16/0833; A61M 16/0875; A61M 16/101; A61M 16/1015; A61M 16/107; A61M 16/12; A61M 2005/1405; A61M 2016/0036; A61M 2016/0042; A61M 2016/1025; A61M 2202/025; A61M 2205/13; A61M 2205/18; A61M 2205/3375; A61M 2205/3553; A61M 2205/3561; A61M 2205/3584; A61M 2205/3592; A61M 2205/502; A61M 2205/52; A61M 2205/581; A61M 2205/583; A61M 2205/584; A61M 2205/587; A61M 2205/8206; A61M 2205/8212; A61M 2209/084; A61M 2210/0618; A61M 2210/1014; A61M 2230/005; A61M 2230/04; A61M 2230/20; A61M 2230/205; A61M 2230/40; A61M 2230/42; A61M 2230/43; A61M 2230/432; A61M 2230/46; A61M 2230/50; A62B 7/02; A62B 9/06; A62B 18/00; A62B 18/02; A62B 18/04; A62B 18/08; A62B 18/082; A62B 23/025; A41D 13/11; A41D 13/1115; A41D 13/1176; A63B 33/00; B63C 11/16; B63C 2011/165; B63C 11/205; B63C 11/207; A61B 2560/0437; A61B 34/25; A61B 5/0013; A61B 5/002; A61B 5/0022; A61B 5/01; A61B 5/0205; A61B 5/02055; A61B 5/021; A61B 5/02152; A61B 5/032; A61B 5/0402; A61B 5/0476; A61B 5/048; A61B 5/0496; A61B 5/08; A61B 5/0803; A61B 5/0833; A61B 5/0836; A61B 5/085; A61B 5/087; A61B 5/0871; A61B 5/091; A61B 5/11; A61B 5/1106; A61B 5/117; A61B 5/145; A61B 5/14532; A61B 5/1455; A61B 5/14551; A61B 5/16; A61B 5/162; A61B 5/411; A61B 5/417; A61B 5/4809; A61B 5/4812; A61B 5/4821; A61B 5/4836; A61B 5/6821; A61B 5/7207; A61B 5/7239; A61B 5/7257; A61B 5/7264; A61B 5/743; A61B 5/7435; A61B 5/746; A61B 5/7465; A61B 6/463; A61B 6/563; A61B 7/04; G06F 19/321; G06F 19/322; G06F 19/327; G06F 19/3406; G06F 19/3418; G06F 19/345; G06F 19/3456; G06F 19/3481; G06F 19/3487; G06F 3/011; G06F 3/048; G06F 3/0482; G06F 3/0484; G06F 3/04842; G06F 3/04847; G06F 3/0489; G06F 9/4446; G06Q 50/22; G06Q 50/24; G08B 25/00; G08B 25/016; G08B 5/22; G08B 5/222; G08B 7/06; G09B 21/00; G09B 21/006
USPC ............ 128/200.24, 202.22, 203.12, 203.14, 128/204.18, 204.21, 204.23, 205.23; 700/17, 83, 84; 702/19; 715/700, 764, 715/771, 781, 808, 809
See application file for complete search history.

(56) References Cited

U.S. PATENT DOCUMENTS

| | | | | |
|---|---|---|---|---|
| 6,349,724 | B1* | 2/2002 | Burton | A61M 16/0057 128/204.18 |
| 6,546,930 | B1* | 4/2003 | Emerson | A61M 16/0051 128/204.18 |
| 7,100,608 | B2* | 9/2006 | Brewer | A61M 16/00 128/204.18 |
| 7,827,038 | B2* | 11/2010 | Richard | A61M 16/06 705/2 |
| 8,195,313 | B1 | 6/2012 | Fadell et al. | |
| 8,424,514 | B2* | 4/2013 | Oates | 128/200.21 |
| 8,944,057 | B2* | 2/2015 | Hill | 128/200.24 |
| 9,072,848 | B2* | 7/2015 | Bertinetti | A61M 16/0051 |
| 2002/0056452 | A1 | 5/2002 | Brewer et al. | |
| 2004/0116784 | A1 | 6/2004 | Gavish | |
| 2008/0071209 | A1 | 3/2008 | Moubayed et al. | |
| 2008/0072902 | A1 | 3/2008 | Selzer et al. | |
| 2008/0078384 | A1* | 4/2008 | Messenger | A61M 16/0051 128/203.12 |
| 2009/0293875 | A1* | 12/2009 | Kwok | A61M 16/0051 128/204.18 |
| 2010/0229867 | A1 | 9/2010 | Bertinetti et al. | |
| 2011/0164002 | A1 | 7/2011 | Hill et al. | |
| 2012/0240933 | A1* | 9/2012 | Haas | A61M 16/06 128/204.21 |

OTHER PUBLICATIONS

Notification of Transmittal of The International Search Report and the Written Opinion of the International Searching Authority dated Oct. 4, 2013 (PCT/US13/39019); 18 Pages.
Extended European Search Report for EP 13 803 951.6. dated Jul. 25, 2016. 11 pages.

* cited by examiner

METHOD AND SYSTEM FOR OPERATING A PATIENT VENTILATION DEVICE

FEDERALLY SPONSORED RESEARCH/DEVELOPMENT

Not Applicable

BACKGROUND

1. Technical Field

The present disclosure relates generally to the treatment of respiratory and cardiovascular conditions, and more particularly to methods and systems for operating or otherwise interacting with a patient ventilation device.

2. Related Art

Sleep apnea is a serious medical condition in which patient breathing during sleep pauses abnormally, or is abnormally low. Apnea is categorized as obstructive, central, and combined obstructive and central, though the obstructive sleep apnea (OSA) is the most common. The patient's upper airway repeatedly narrows or collapses, causing pauses in breathing that may extend in duration up to half a minute. Although some degree of apnea is considered normal, in more severe cases, daytime sleepiness and fatigue may result as a consequence of reduced blood oxygen saturation, as well as constant interruptions to sleep cycles resulting from patients gasping for air. There have been studies linking sleep apnea to more severe long-term health issues including heart disease and depression, and recently, to cancer as well. With apnea being strongly linked to obesity, and with obesity being projected to increase, the number of patients suffering from sleep apnea is likely to increase concomitantly.

One common treatment for obstructive sleep apnea is continuous positive airway pressure (CPAP) therapy, where a positive pressure is applied to the patient's airway to prevent its collapse as would otherwise occur during an apnea episode. By retaining the patient's airway, normal, uninterrupted breathing during sleep is ensured. In a basic implementation, CPAP therapy applies a constant pressure that is not tied to the patient's normal breathing cycle. The positive airway pressure is desired in the inspiratory phase when the pressure differences between the lungs and the nose contribute to the collapse of the intermediate airway. Various improvements have been developed that reduce positive pressure flow to the patient during the expiratory phase, thereby reducing resistance to the patient's breathing efforts and patient discomfort. Further refinements that recognize the minimal flow and pressure toward the end of the patient's expiratory phase and responsively reduce the delivery of positive pressure have also been contemplated.

Earlier patient breathing assistance devices tended to be uncomfortable to use, not only for its bulkiness with respect to the patient interface or mask, but as mentioned above, the reduced accuracy of the control algorithms that resulted in the misapplication of patient pressure. With these issues being resolved, or at least being significantly improved upon, what was previously prescribed only for the more severe cases of sleep apnea in which the benefits of treatment outweighed the significant discomfort is now useful for treating a wider spectrum of sleep apnea conditions. Further cost reductions were possible with the elimination of expensive flow sensors and control systems based thereon in favor of pressure sensor based systems such as that described in U.S. patent application Ser. No. 13/411,257 entitled "DUAL PRESSURE SENSOR CONTINUOUS POSITIVE AIRWAY PRESSURE (CPAP) THERAPY," filed Mar. 2, 2012, the disclosure of which is hereby incorporated by reference in its entirety herein. Coupled with improved performance, these and numerous other cost reduction efforts, CPAP devices are becoming increasingly accessible to many more patients, especially for home use.

Being that CPAP devices are largely derived from medical ventilator devices utilized in clinical settings, its operating interface has accordingly been geared more towards doctors, nurses, technicians, and other medical professionals. That is, many configuration settings, some of which may require numeric values, are immediately presented on startup before a therapy session can be started. While these settings and other operational details may be readily recognized by skilled medical personnel who are familiar with CPAP treatment and obstructive sleep apnea conditions, this is not necessarily the case with individual patients. Since medical personnel cannot always be present to operate CPAP devices at home, patients may face the difficult task of configuring and setting up the prescribed treatment alone. Furthermore, the seemingly simple step of activating and using the CPAP device each night may be complicated due to the multi-level nested menus of conventional solutions. Such frustrations encountered during use may discourage some patients from continuing treatment.

Accordingly, there is a need in the art for improved methods and systems for operating a patient breathing apparatus. It would be desirable to present a minimal number of options that could potentially be misconfigured while maintaining the requisite functionality. There is also a need for CPAP device user interfaces that are more user-friendly and encourage regular treatment.

BRIEF SUMMARY

In accordance with one embodiment of the present disclosure, there is contemplated a method for operating a patient ventilation device. The device may include a display interface and a ventilation source that is pneumatically coupled to a patient. The method may include generating a device activation user element on the display interface. The device activation user element may be displayed substantially dominantly on the display interface. There may also be a step of detecting at least one of an input received on an input device that corresponds to a selection of the device activation user element and an activation of the ventilation source by an initiation of treatment of the patient according to one or more treatment configuration settings. Additionally, the method may include generating a patient interface fitment feedback indicator and a treatment screen on the display interface. This may be in response to the one of the detected input received on the input device and the detected activation of the ventilation source. The treatment screen may include one or more modifiable user interface elements that each show predefined values and may correspond to the one or more treatment configuration settings. The generating of the device activation user element, the treatment screen, the patient interface fitment feedback indicator and any display transitions between may be exclusive in the absence of further input received on the input device.

Another embodiment of a method for operating a patient ventilation device is contemplated. The method may include generating a patient interface fitment feedback indicator on the display interface. Additionally, a treatment screen may be generated. The treatment screen can include one or more modifiable user interface elements each showing predefined values and corresponding to one or more treatment configuration settings. The ventilation source may be activated to initiate treatment of the patient. The step may also include generating a treatment continuation user element. The method may further include detecting at least one of an input received on an input device corresponding to a selection of the treatment continuation user element and an expiration of a time out period. There may also be a step of generating, notwithstanding the detected at least one of the input received on the input device and the expiration of the time out period, the patient interface fitment feedback indicator. Furthermore, the method may include generating a treatment status screen in response to the detected at least one of the input received on the input device and the expiration of the time out period.

A method for suspending treatment in a patient ventilation device is also envisioned. Again, like the aforementioned embodiments, the patient ventilation device may include a display interface and a ventilation source pneumatically coupled to a patient. The method may include detecting at least one of an input received on an input device corresponding to a selection of a treatment suspension user element and a first modification to a pneumatic circuit between the patient and the ventilation source from a first condition to a second condition. Furthermore, there may be a step of generating a treatment suspension screen on the display interface, this may be in response to detecting the at least one of the input and the modification to the pneumatic circuit. The treatment suspension screen may include a set of usage statistics data and a preselected patient motivational message that corresponds to specific values of the set of usage statistics data. No other content aside from the treatment suspension screen may be generated on the display interface following the detecting the at least one of the input and the modification to the pneumatic circuit.

There is also contemplated a method for concluding treatment in a patient ventilation device. As with the foregoing alternative embodiments of the present disclosure, the patient ventilation device may include a display interface and a ventilation source pneumatically coupled to a patient. The method may include detecting at least one of an input received on an input device corresponding to a selection of the treatment termination user element and a deactivation of the ventilation source. There may also be a step of generating on the display interface a treatment conclusion screen in response to the detecting the at least one of the input and the deactivation of the ventilation source. The treatment conclusion screen may include a set of usage statistics data and a preselected patient motivational message corresponding to specific values of the set of usage statistics data. No other content aside from the treatment conclusion screen may be generated on the display interface following the detecting the at least one of the input and the deactivation of the ventilation source.

Another embodiment of the present disclosure contemplates a patient ventilation system. There may be a patient ventilation interface, as well as a ventilation source pneumatically coupled to a patient over the patient ventilation interface. Further, the system may include a pressure controller that regulates airflow delivery from the ventilation source to the patient according to one or more predefined treatment configuration settings. The pressure controller may have an inactive ventilation state, a ventilation initiation state, a treatment state, and a ventilation deactivation state. There may additionally be an input interface and a display interface that are coupled to the pressure controller. The display interface may be configured to generate, exclusively, a device activation user element with the pressure controller in the inactive ventilation state, a fitment feedback indicator and a treatment screen in a ventilation initiation state, the fitment feedback indicator and a treatment status screen in the treatment state, and a treatment conclusion screen in the ventilation deactivation state.

The present invention will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which.

Common reference numerals are used throughout the drawings and the detailed description to indicate the same elements.

DETAILED DESCRIPTION

The detailed description set forth below in connection with the appended drawings is intended as a description of the presently contemplated embodiments of the methods and systems for operating a patient ventilation device and is not intended to represent the only form in which the disclosed invention may be developed or utilized. Generally, the device is understood to deliver breathing gas to a patient for the treatment of obstructive sleep apnea (OSA) and other cardio-pulmonary conditions, and selectively augments and relieves pressure throughout the breathing cycle. The present disclosure contemplates various methods of operating such a device. The description sets forth the various functions and features in connection with the illustrated embodiments. It is to be understood, however, that the same or equivalent functions may be accomplished by different embodiments that are also intended to be encompassed within the scope of the present disclosure. It is further understood that the use of relational terms such as first and second and the like are used solely to distinguish one from another entity without necessarily requiring or implying any actual such relationship or order between such entities.

Figure 1:
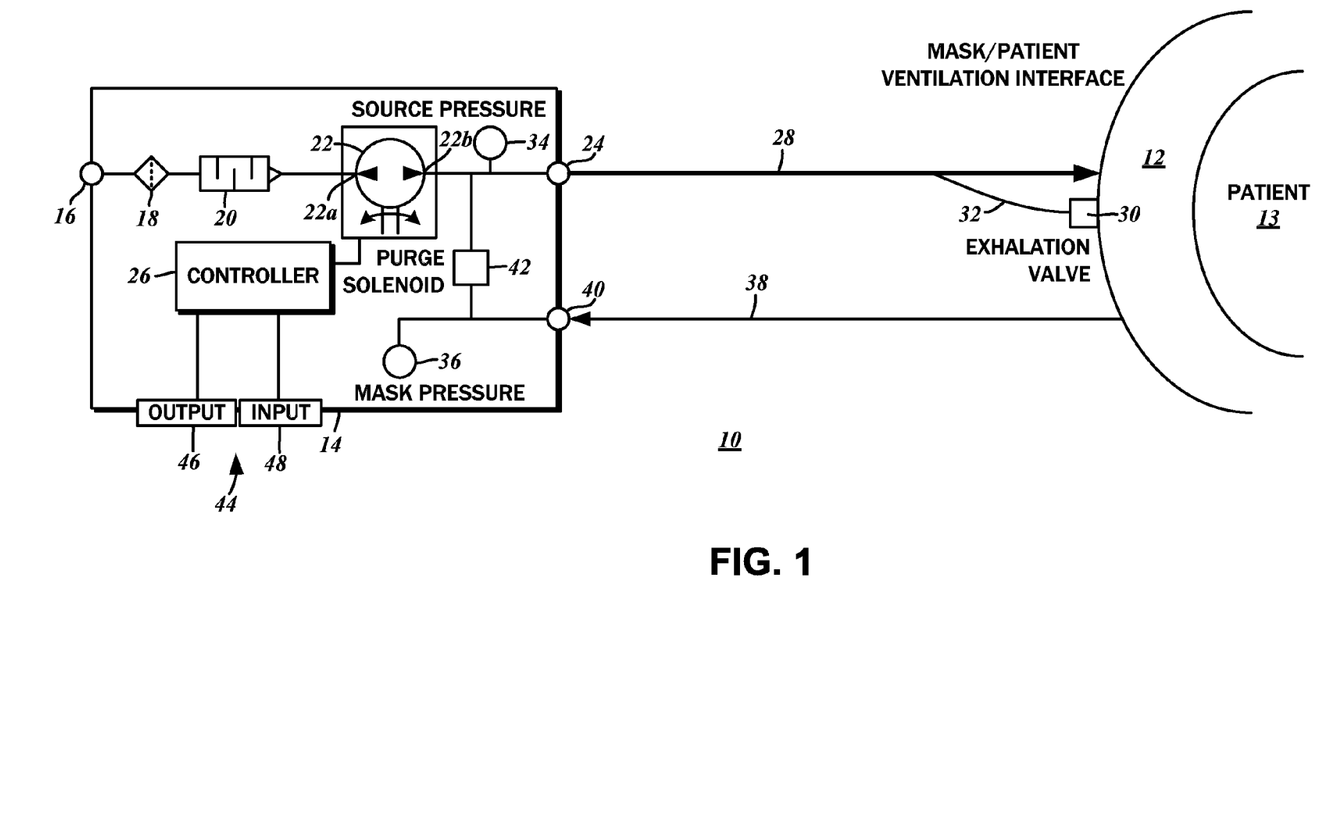
FIG. 1 is a block diagram illustrating various components of an exemplary patient ventilation system, particularly, a CPAP device, including a typical ventilation unit, a patient interface, and gas passage conduits.

The block diagram of FIG. 1 illustrates an exemplary patient ventilation system 10 in which various embodiments of the present disclosure may be implemented. There is a mask or patient ventilation interface 12, and a ventilation unit 14. The following disclosure will make reference to the patient ventilation interface 12 and the mask interchangeably. It is understood to be an apparatus such as a full-face mask or a nasal pillows mask that can be placed in direct gas flow communication with the upper respiratory tract, i.e., the nasal cavity and/or the oral cavity, of a patient 13. One possible mask is disclosed in U.S. patent application Ser. No. 13/411,348 entitled VENTILATION MASK WITH INTEGRATED PILOTED EXHALATION VALVE filed Mar. 2, 2012, now issued U.S. Pat. No. 8,844,533, and U.S. patent application Ser. No. 13/411,407 entitled VENTILATION MASK WITH INTEGRATED PILOTED EXHALATION VALVE filed Mar. 2, 2012, now issued U.S. Pat. No. 8,839,791, the disclosures of which are hereby incorporated by reference in their entireties herein. It will be appreciated that other apparatuses that so interface the respiratory tract of the patient 13 to the ventilation unit 14 may be substituted without departing from the scope of the present disclosure.

The ventilation unit 14 generates a flow of breathing gas that is delivered to the patient via the patient ventilation interface 12. The breathing gas may be ambient air, a combination of ambient air enriched with oxygen, or any other suitable mixture of gas appropriate for treating the patient. Those having ordinary skill in the art will recognize the variety of options for mixing breathing gasses before delivery to the patient. In further detail, the ventilation unit 14 includes a first inlet port 16, through which ambient air is drawn. The first inlet port 16 is in communication with an inlet filter 18 that removes particulates and other contaminants from the breathing gas that is ultimately delivered to the patient. Optionally, in line with the inlet filter 18 is a sound suppressor 20 that reduces the sound of gas flow through the ventilation unit 14.

The force needed for drawing the ambient air through the first inlet port 16, the inlet filter 18, and the sound suppressor 20 is provided by a ventilation source 22, which may be a centrifugal fan, blower, or any other suitable device that generates gas flow and pressure suitable for CPAP treatment in accordance with the present disclosure. The ventilation source 22 has an inlet port 22a coupled to the sound suppressor 20, and an outlet port 22b that is in gas flow communication with an outlet port 24 of the ventilation unit 14. The ventilation source 22 is driven electrically and its actuation is governed by a controller 26, which implements various methods of CPAP treatment such as those disclosed in the aforementioned co-pending U.S. patent application Ser. No. 13/411,257.

The flow of breathing gas that is output from the ventilation source 22 is passed through the outlet port 24 to a gas conduit 28 that is in coupled to the aforementioned patient ventilation interface 12. The gas conduit 28 is understood to be a plastic tube having a predetermined inner diameter such as 22 mm or smaller, though any other conduit of suitable material and construction may be utilized. The patient ventilation interface 12 in accordance with various embodiments of the present disclosure also includes a piloted exhalation valve 30 that is selectively actuated depending on the pressure differential between the patient ventilation interface 12 and the ventilation unit 14. The piloted exhalation valve 30 is connected to a pilot line 32 that branches from the gas conduit 28. A pressure difference is generated between the patient ventilation interface and the exhalation valve, such that it is closed during inspiration and opened during expiration. It will be appreciated that the specifics of the patient ventilation interface 12, including the piloted exhalation valve 30 thereof, are presented by way of example only and not of limitation. Any other suitable patient ventilation interface 12, including those that may be utilized in conjunction with different variations of the ventilation unit 14, may be substituted without departing from the scope of the present disclosure.

In order to ascertain such pressure differentials, the presently contemplated patient ventilation system 10 includes dual pressure sensors, including a source pressure sensor 34 and a patient interface pressure sensor 36. The source pressure sensor 34 is disposed within the ventilation unit 14, and monitors the pressure at the outlet port 22b. The patient interface pressure sensor 36 is also physically disposed within the ventilation unit 14, but is in direct gas flow communication with the patient ventilation interface 12 over a pressure sensor line 38 that is connected to a second inlet port 40. When the ventilation unit 14 is operating, gas pressure within the pressure sensor line 38 as well as the gas conduit 28 may be connected to deliver a purge flow to clear line 38. This can be done through a purge solenoid 42 connected to both. The purge can be continuous or intermittent according to the patient's breathing phase or pressure difference between the blower pressure and the mask pressure.

As indicated above, the sequence and timing of delivering gas flow to the patient 13 are governed by the specific treatment modalities that utilize feedback data from the pressure sensors 34, 36. The setting of options relating to the treatment modalities, along with the starting and stopping of treatment is possible via a user interface 44 coupled to the controller 26, which includes an output or display interface 46, as well as an input interface 48. Further details pertaining thereto, including possible methods of operation will be described more fully below.

Figure 2:
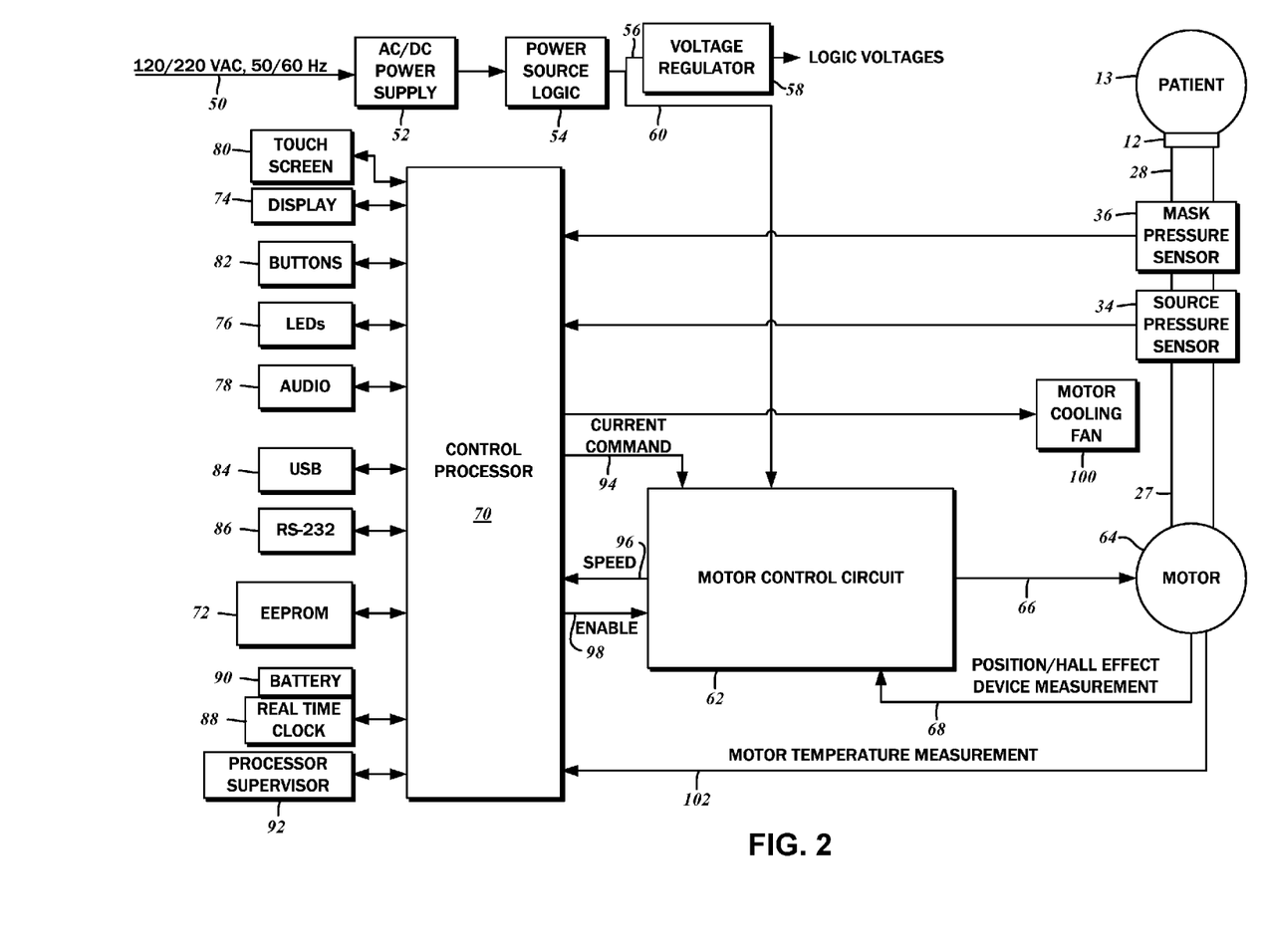
FIG. 2 is a block diagram illustrating the electrical components of the ventilation unit.

The block diagram of FIG. 2 illustrates the various electrical components of one typical embodiment of the ventilation unit 14. Power for the ventilation unit 14 may be provided from a conventional household electricity supply of either 120V or 220V alternating current (AC), at 50 Hz or 60 Hz. The block diagram denotes this supply as a power source 50. A power supply 52 is connected to the power source 50, and as will be recognized by those having ordinary skill in the art, the power signal is variously rectified, filtered, and stepped down to a direct current (DC) voltage. In accordance with one embodiment of the present disclosure, the DC voltage source is 24 V. It is understood that the ventilation source 22 utilizes a higher DC voltage than control logic devices, and thus the power supply 52 is connected to a power source logic 54. A first output 56 of the power source logic 54 is connected to an integrated circuit voltage regulator 58 that steps down the DC voltage to the logic device level of 5V. A second output 60 of the power source logic 54 is the existing high DC voltage directly from the power supply 52, and is connected to a motor control circuit 62.

The ventilation source 22 is comprised of several electrical components, including a motor 64 and the aforementioned motor control circuit 62. In accordance with one embodiment, the motor 64 is a brushless DC or electrically commutated motor. It will be recognized that the speed of rotation of the motor 64 is based upon input logic signals provided to the motor control circuit 62, which drives electrical current through its windings that induce magnetic fields that translate to rotational motion of the attached rotor. A fan coupled to the rotor thus rotates and generates a flow of air through an internal conduit 27. The internal conduit 27 is coupled to the outlet port 24, which is coupled to the gas conduit 28. As described above, the source pressure sensor 34 and the patient interface pressure sensor 36 are connected to the pneumatic circuit between the motor 64 and the patient 13.

The motor control circuit 62 has a motor drive output 66 that is connected to the motor 64. The rotational position of the motor 64 is detected by a Hall-effect sensor that is incorporated into the motor 64. An output voltage 68 from the Hall-effect sensor is fed back to the motor control circuit 62, which ensures that the actual position corresponds to the intended or commanded position.

The controller 26 and its functionality may be implemented with a programmable integrated circuit device such as a microcontroller or control processor 70. Broadly, the control processor 70 receives certain inputs, and based upon those inputs, generates certain outputs. The specific operations that are performed on the inputs may be programmed as instructions that are executed by the control processor 70. In this regard, the control processor 70 may include an arithmetic/logic unit (ALU), various registers, and input/output ports. Although external memory such as EEPROM (electrically erasable/programmable read only memory) 71 may be connected to the control processor 70 for permanent storage and retrieval of program instructions, there may also be an internal random access memory (RAM). One embodiment contemplates the use of an Intel 8081 instruction set/architecture, though any other suitable instruction set or processor architecture may be substituted. As indicated above, the control processor 70 is powered by a low voltage DC supply from the voltage regulator 58.

As mentioned above, in order to set the operational parameters of the ventilation unit, and to initiate or terminate certain functions, a graphical user interface is provided. Such graphical user interface is generated on a display screen 74, which may be of a liquid crystal display (LCD) type. Any type of graphic may be shown on the display screen 74, though for more specific indicators, a simple light emitting diode (LED) device 76 may be utilized. It will be recognized that alarm conditions, power status, and the like may be indicated with the LED device 76. Audible outputs may also be produced with audio transducers 78 that are likewise connected to the control processor 70. Among the contemplated outputs that may be generated on the audio transducer 78 include simple beeps and alarms, as well as sophisticated voice prompts that provide information and instructions.

An operator may interact with the graphical user interface through different input devices such as a touch screen interface 80 that is overlaid on the display screen 72. It will be recognized that various graphic elements may be generated on the display screen 72, with touch inputs/interactions corresponding in position to those graphic elements being evaluated as a selection or activation of the same. Various touch screen interfaces, some of which may be directly integrated with the display screen 72, are known in the art. Besides touch screen inputs, buttons 82 may also be connected to the control processor 70 for similarly receiving user inputs. It is understood that the audio transducer 78 may also accept sound input in the form of voice commands, the processing of which is performed may be performed by the control processor 70.

Several modalities for connecting to and communicating with other data processing devices such as general-purpose computers are also contemplated. Accordingly, the control processor 70 may be connected to a universal serial bus (USB) controller 84. For more basic communications, there may be a serial RS-232 transceiver 86. Through these data communications modalities, the configuration options of the ventilation unit 14 may be set, operating profiles may be downloaded, and so forth. Notwithstanding the specific reference to USB and RS-232 communications modalities, any other communications modality including wireless systems may be substituted without departing from the present disclosure.

The functions of the ventilation unit 14 depend on proper synchronization, and so the control processor 70 is connected to a real time clock 88 that maintains a common clock cycle. Although a primary feature of the real time clock 88 is to maintain synchrony at a processor cycle level, longer term time data is also maintained. In order to retain such time data, the real time clock 88 may be powered independently of the primary power source 50, and there is accordingly a battery backup 90. Under heavy processing loads or unexpected program conditions, the control processor 70 may become unable to execute critical programmed steps in real-time. Thus, the control processor 70 may include a processor supervisor 92 that invokes a program execution break upon detecting such conditions. Typically, this is implemented as a step of clearing a memory variable periodically, and when that step is unable to take place because instruction execution is frozen or otherwise delayed, the processor supervisor 92 may cause a predetermined routine to be executed.

As mentioned above, the motor 64 is driven by the motor control circuit 62, which generates different outputs depending on signals received from the control processor 70. The signal to drive the motor 64 is generated on a current command line 94. For control processing on a broader level, feedback from the ventilation source 22 is utilized, and in the specific form of a speed or current measurement input 96 from the motor control circuit 62. Furthermore, as detailed below, pressure readings at the ventilation source 22 and the patient 13 are utilized to reach control decisions. Accordingly, the source pressure sensor 34 and the patient interface pressure sensor 36 are both connected to the control processor 70. The ventilation source 22 is activated and deactivated via a motor enable line 98. To ensure that the temperature of the motor 64 remains within operational parameters, a motor cooling fan 100 may be driven directly by the control processor 70. In some embodiments, there may be additional control circuitry that isolates the power source of the motor cooling fan 100 from the control processor 70. The decision to activate and deactivate the motor cooling fan 100 may be made in response to temperature readings from the motor 64, and so there is a motor temperature reading 102 passed to the control processor 70.

Notwithstanding the foregoing description of the particular patient ventilation system 10, the contemplated method of operation and a system configured for such operation can be adapted to any other patient ventilation system 10. Those having ordinary skill in the art will recognize the modifications to be made for such adaptation. Generally, the present disclosure contemplates the operation of the patient ventilation system 10, including the starting, suspending, and stopping of treatment, and configuring certain treatment options, by the patient 13, rather than a clinician. In this regard, the interface and associated operating methods are envisioned to be user-friendly and uncomplicated so that no special expertise is required, and does not discourage the patient 13 from further continued use.

Figure 3:
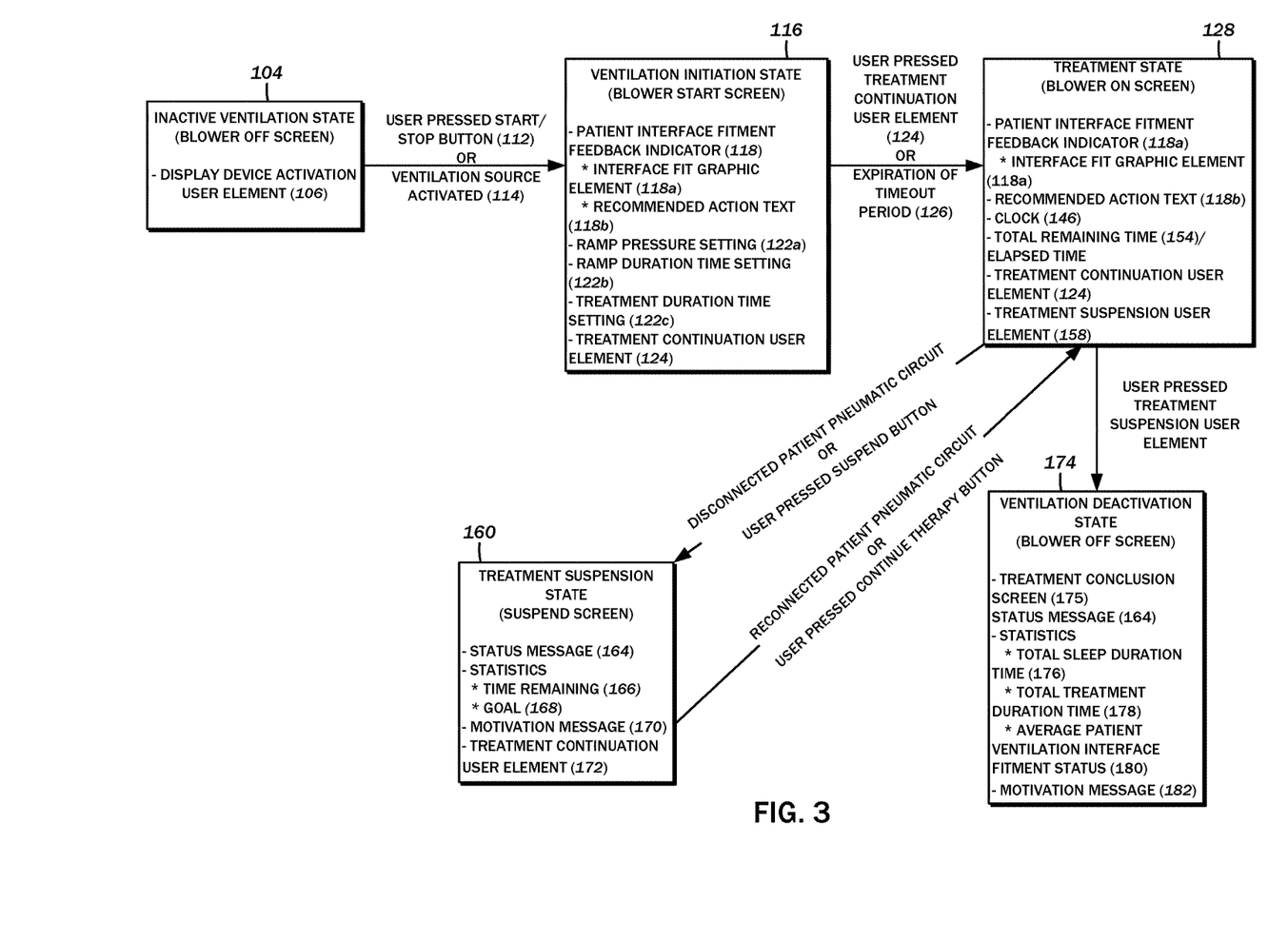
FIG. 3 is a state diagram showing the various user interface states contemplated for the patient ventilation system.

Referring now to the state diagram of FIG. 3, the patient ventilation system 10 may initially be in an inactive ventilation state 104. When the ventilation unit 14 is completely powered off, all but the components powered by the backup battery 90 may be deactivated. The system may be turned on by activating a master power switch. Following basic housekeeping tasks such as boot up, loading instructions from memory, and beginning execution of such instructions, the controller 26, and more generally the patient ventilation system 10, may enter the inactive ventilation state 104.

Figure 4:
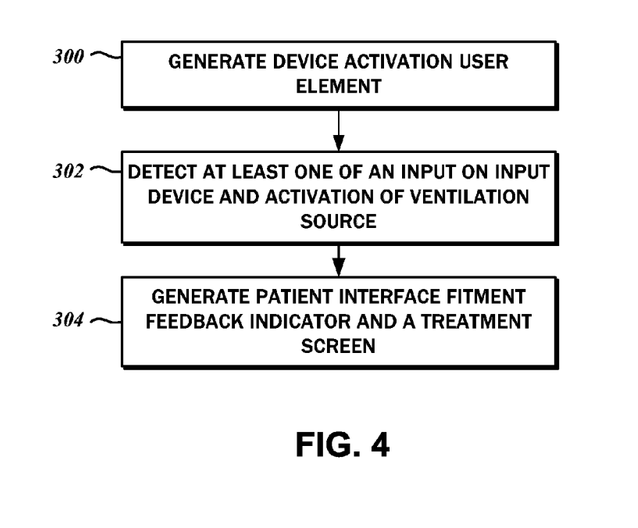
FIG. 4 is a flowchart illustrating one embodiment of the method for operating the patient ventilation system by which the system transitions from an inactive state to a ventilation initiation state.
Figure 5:
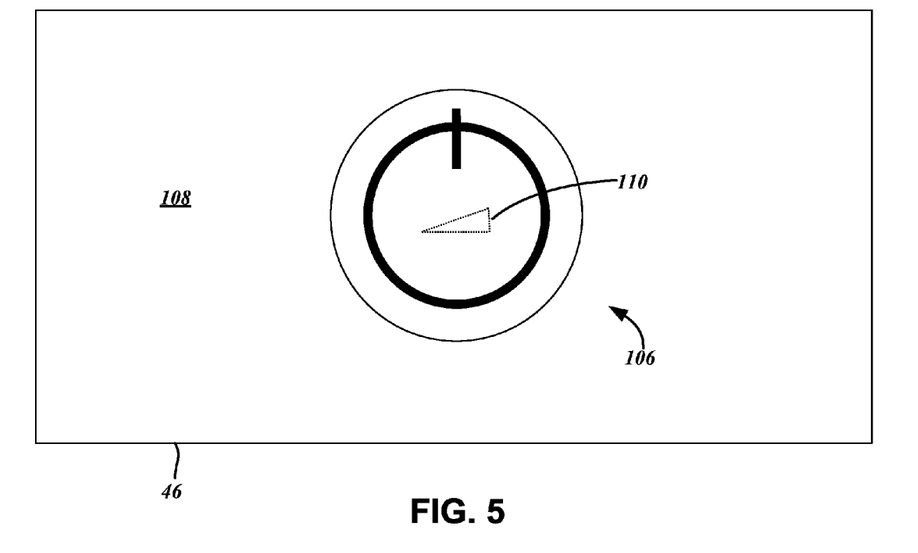
FIG. 5 is an example embodiment of a device activation user element.

As shown in the flowchart of FIG. 4, one method for operating the patient ventilation system 10 includes a step 300 of generating a device activation user element 106 on the display interface 46. This may also be referred to as a "blower off" screen. FIG. 5 is an exemplary screen capture of the display interface 46 with a primary display area 108 on which various graphic elements may be generated and shown. Overlaid on the primary display area 108 is the device activation user element 106. The specific appearance of the device activation user element 106 may vary, though in the example shown, it is a circle with an intersecting line as is typical with other power button type interface graphics common across many different types of devices. Although shown in black, the circle and line may be colored red to further denote that the patient ventilation system 10 is in a substantially deactivated state, also consistent with user interface elements of other electronic devices. Along these lines, various animation effects may also be applied to the device activation user element 106 such as pulsating intensities, movement of secondary elements, and so forth. As will be described in further detail below, a ramp graphic 110 may be included, denoting that the patient ventilation system 10 will respond with slowly ramping up the airflow delivery upon invoking the device activation user element 106.

In some embodiments, the device activation user element 106 is the only graphical element shown on the display interface 46 at any instance, while in others, there may be other graphical elements that are also shown concurrently. Where other graphical elements are displayed, it is understood that the device activation user element 106 is substantially dominantly displayed, i.e., as the largest, the most vibrant, or the most prominent element, or occupies most of the primary display area 108. Where different graphics are cycled, the substantially dominant display of the device activation user element 106 may mean that its display is active a majority of the time in relation to others, either alone or in combination. For example, this could entail generating a first graphic element or graphical sequence for approximately 25% of the time, while generating the device activation user element 106 for approximately 75% of the time. Additionally, this could also entail, for example, generating a first graphic element or graphical sequence for approximately 30% of the time, generating a second graphic element or graphical sequence for another approximately 30% of the time, and generating the device activation user element 106 for approximately 40% of the time. Those having ordinary skill in the art will recognize various other presentations of the device activation user element 106 that would be substantially dominant, and each such presentation is deemed to be within the scope of the present disclosure.

The method may continue with a step 302 of detecting at least one of an input on the input interface 48 and an activation of the ventilation source 22. As indicated above, the user interface 44 may be a touch screen with an input panel overlaid on or integrated with the display interface 46. In this case, the input received on the input interface 48 may correspond spatially to a display position of the device activation user element 106. In other words, the patient 13 may "touch" the device activation user element 106 as displayed on the user interface 44. Alternatively, various buttons 82 that correspond to a selection of the device activation user element 106 is also contemplated. In general, with reference again to the state diagram of FIG. 3, such selection, e.g., the user pressing the start/stop button per step 112, is understood to begin therapy of the patient, and transitions the controller 26 to a ventilation initiation state 116, where gas flow delivery or treatment is initiated.

In some embodiments, it is possible to transition to the ventilation initiation state 116 without selecting the device activation user element 106. More particularly, completing the connection of the patient-ventilator circuit by securing the mask or patient ventilation interface 12 to the patient 13, and the detection of the patient 13 starting or continuing a breathing cycle, is also operative to invoke the aforementioned state transition, thereby activating the ventilation source per step 114 and initiating treatment of the patient 13. Various techniques are known in the art to detect patient breathing cycles and the specific location within that cycle, and any one may be substituted without departing from the scope of the present disclosure.

The initial gas flow delivery to the patient 13 is in accordance with one or more treatment configuration settings, which may be preset for the specific patient 13. These configuration options are also modifiable in the ventilation initiation state 116. In this regard, the method continues with a step 304 of generating a patient interface fitment feedback indicator 118 and a treatment screen 120 on the display interface 46. This step is understood to be in response to detecting the activation of at least one of the device activation user element 106 and the activation of the ventilation source 22 by virtue of detecting patient breathing and initiating treatment.

Figure 6:
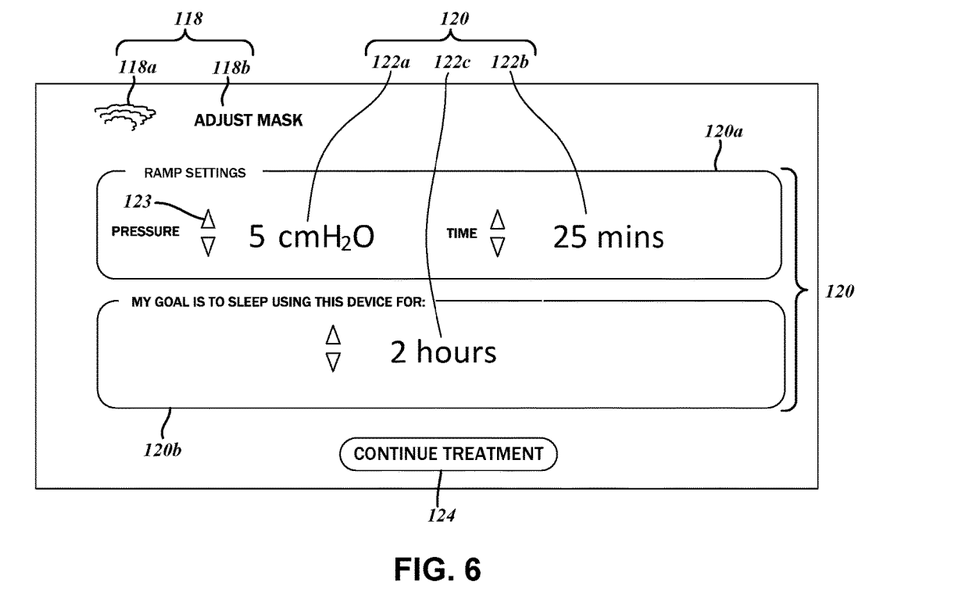
FIG. 6 is an example embodiment of a treatment screen and a patient interface fitment feedback indicator.

FIG. 6 depicts an example implementation of the patient interface fitment feedback indicator 118 and the treatment screen 120. The patient interface fitment feedback indicator 118 is understood to generally show the fit of the ventilation interface 12 to the patient 13. One technique involves a determination of fit (too lose, correct, too tight) based on the amount of leak calculated from pressure readings at the patient ventilation interface 12 and at the ventilation source 22. This particular modality is disclosed in the present applicant's co-pending U.S. patent application Ser. No. 13/441,607 entitled MECHANICAL VENTILATION MASK FIT STATUS INDICATION filed on Apr. 4, 2012 and the disclosure of which is hereby incorporated by reference in its entirety herein. However, other leak modalities of leak detection may also be utilized.

The patient interface fitment feedback indicator 118 may include an interface fit graphic element 118a that illustrates simply whether the patient ventilation interface 12 is fitted too tightly, correctly, or too loosely, and may include further gradients corresponding to further degrees of fit. Various other graphical illustration modalities are contemplated and disclosed, and may be substituted without departing from the present disclosure.

Additionally, the patient interface fitment feedback indicator 118 may include a recommended action text 118b, which instructs or otherwise suggests to the patient 13 on what to do to improve the fit of the ventilation interface 12.

In the illustrated example, the recommended action text 118b merely reads "adjust mask," though more detailed actions such as "tighten mask," "loosen mask," slightly shift mask around for comfort," and the like may also be utilized.

The treatment screen 120 includes one or more modifiable user interface elements 122, each of which show predefined values of the treatment configuration settings. In further detail, the treatment screen 120 is segregated into a ramp settings segment 120a and a treatment duration segment 120b. The ramp settings segment 120a includes a ramp pressure setting 122a and a ramp duration time setting 122b, while the treatment duration segment 120b includes a treatment duration time setting 122c. Each of the settings may be adjusted incrementally using the upward and downward arrow graphic elements 123, though it is possible to substitute other input modalities with which specific numeric values can be entered.

Generally, ramping refers to the gradual increase of delivered gas flow to the patient 13 from a minimum level to a prescription level. As will be appreciated by those having ordinary skill in the art, during waking moments it is desirable to minimize delivered gas flow because splinting pressure tends to cause discomfort and prevent the patient 13 from falling asleep. Once the patient reaches a sufficiently deep level of sleep, slightly increased splinting pressure does not cause any disruptions. Thus, in the beginning of the treatment or ramp start when the patient 13 is still awake, gas flow is minimized, while at the ramp end when the patient 13 is presumably asleep, gas flow is at the prescribed level to prevent obstructive sleep apnea. The pressure increase interval is set in the ramp pressure setting 122a, and the length of the ramp (from ramp start to ramp end) is set in the ramp time setting 122b.

The patient 13 can also set the length of time for the current treatment underway. It will be recognized that while the patient ventilation system 10 is useful for helping the patient 13 sleep without apnea episodes, when first starting treatment, there may be some level of discomfort. Thus, it may be desirable to slowly increase the treatment duration over multiple nights to help the patient 13 gradually acclimate to the sensations associated with the splinting pressure. As such, the treatment duration time setting 122c can be modified.

In one of the contemplated methods, the display interface 46 is generally limited to showing just the device activation user element 106, the treatment screen 120, and the patient interface fitment feedback indicator 118. In other words, the display of these graphical elements is exclusive, at least in the absence of further input received on the input interface 48 as will be described in further detail below. Some embodiments also contemplate transition effects between these various displays. Thus, it is contemplated that no other graphics or content is shown between the display of the device activation user element 106 in the inactive ventilation state 104 and the display of the treatment screen 120 and the patient interface fitment feedback indicator 118 in the ventilation initiation state 116, except for any transitions between the two states.

Figure 7:
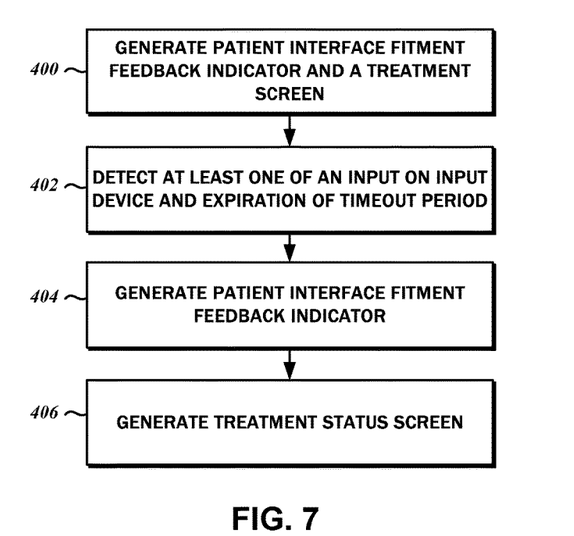
FIG. 7 is a flowchart illustrating another embodiment of the method for operating the patient ventilation system by which the system transitions from the ventilation initiation state to a treatment state.

The flowchart of FIG. 7 illustrates another method for operating the patient ventilation system 10 that begins with the ventilation initiation state 116. The method includes a step 400 of generating the patient interface fitment feedback indicator 118 and the treatment screen 120, also referred to as a "blower start" screen. At this point, it is understood that the treatment of the patient 13 has been initiated, and the ventilation source 22 is delivering gas flow. The treatment screen 120 may also include a treatment continuation user element 124, which can be also be selected via touch input in the manner described above. In a step 402, the method may include detecting at least one of the input received on the input interface 48, and an expiration of a timeout period 126 without any additional input or other external stimulus. This is operative to switch the state of the controller 26 to a treatment state 128.

Regardless of the timeout period or the activation/input of the treatment continuation user element 124, the method includes a step 404 of continuing to generate the patient interface fitment feedback indicator 118. Thus, it is contemplated that whenever the patient ventilation interface 12 is connected to the patient 13 and the ventilation source 22 is delivering gas flow to the same, the patient interface fitment feedback indicator 118 is generated and updated.

Figure 8A:
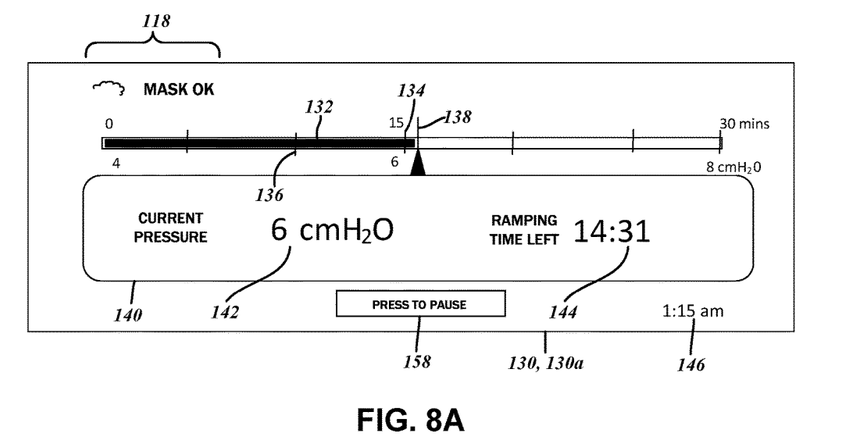
FIG. 8A is one example embodiment of a treatment status screen and the patient interface fitment feedback indicator.

As best shown in the screen capture of FIG. 8A, in the treatment state 128, a treatment status screen 130, also referred to as a "blower on" screen, is generated in accordance with a step 406. In accordance with one embodiment of the present disclosure, during the initial phase of treatment while the delivery pressure is being ramped up, there is a first variation 130a that is shown. More particularly, the ramping process is depicted in a progress bar 132 with a first scale 134 showing the increments of ramp time relative to the total ramp time as set in the ramp duration time setting 122b, and a second scale 136 showing the increments of ramp pressures relative to the final ramp pressure set in the ramp pressure setting 122a. A moving indicator 138 denotes the current ramp time/pressure, with the elapsed portion of the progress bar 132 being filled in to denote completion. The treatment status screen 130 also includes a numerical values segment 140 in which the specific numeric value of the current ramp pressure 142 is shown, along with the current remaining ramp time 144. Furthermore, a clock 146 may be displayed.

Figure 8B:
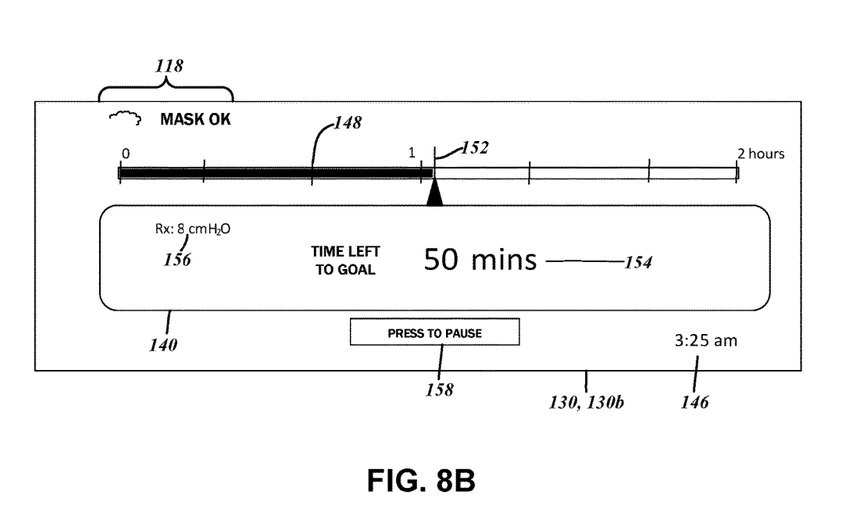
FIG. 8B is another example embodiment of the treatment status screen and the patient interface fitment feedback indicator.

Once the ramping has completed and the ventilation source 22 is delivering the full prescription pressure to the patient 13, a second variation 130b as depicted in FIG. 8B is generated on the display interface 46. Like the first variation 130b, the patient interface fitment feedback indicator 118 is also generated and updated. Although a progress bar 148 is generated, it is understood to indicate treatment progress rather than ramping progress. The time scale 150 shows the increments of treatment time relative to the total treatment time as set in the treatment duration time setting 122c. A moving indicator 152 shows the current treatment time with respect to the time scale 150. In a numerical values segment 140, the total remaining time 154 (a countdown timer) is shown, along with the prescription pressure value 156. As an alternative to the total remaining time 154, the total elapsed time may also be shown. Again, the clock 146 is displayed.

It is possible for the patient 13 to pause or suspend treatment in accordance with another embodiment of the present disclosure. For example, in the middle of sleep, the patient 13 may experience a desire to expel waste material, to eat, to drink, and so forth. In order to be able to perform such functions, it may become necessary to disengage the patient ventilation interface 12. Before doing so, it is possible for the patient 13 to manually input the suspension of the treatment via a pause or suspend button, also referred to as a treatment suspension user element 158 that is generated on the treatment status screen 130. Alternatively, the patient 13 may immediately disconnect the patient circuit from the ventilation source 22, either at the patient ventilation interface 12, at the ventilation unit 14 itself, or anywhere else along the patient circuit. When this occurs, it is understood that the controller 26 detects a modification to the pneumatic circuit between the ventilation unit 14 and the patient ventilation interface 12 in accordance with one of several possible techniques therefor. As referenced herein, modification to the pneumatic circuit is understood to involve, in addition to the foregoing disconnection of the patient ventilation interface 12 from the patient 13, any obstructions that are introduced therein, and any other change that results in a significantly greater or lesser amount of gas delivery to the patient 13.

Figure 9:
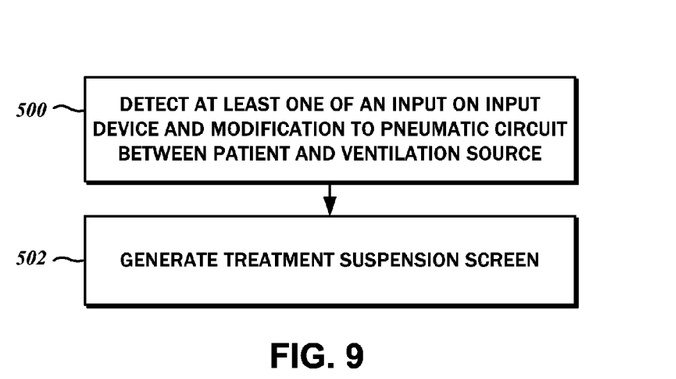
FIG. 9 is a flowchart illustrating an embodiment of a method for suspending the patient ventilation system by which the system transitions from the treatment state to a treatment suspension state.
Figure 10:
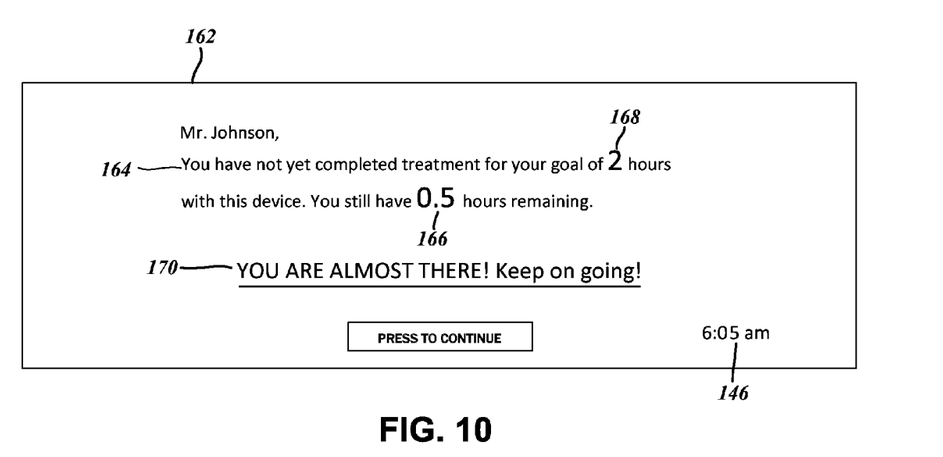
FIG. 10 is an example embodiment of a treatment suspension screen.

Thus, with reference to the flowchart of FIG. 9, a method for suspending treatment is contemplated as involving a step 500 of detecting at least one of an input on the input device, i.e., one that corresponds to the selection of the treatment suspension user element 158, and a modification to the pneumatic circuit between the patient 13 and the ventilation source 22. This transitions the controller 26 to a treatment suspension state 160 where a treatment suspension screen 162 is generated according to a step 502. An example embodiment is shown in FIG. 10, which warns the patient 13 that treatment is not yet complete in a status message 164. Some usage statistics are shown, for example, that there is some time remaining 166 to reach the goal 168 set in the treatment duration time setting 122c. Preferably, though optionally, a motivation message 170 encouraging the patient 13 to continue treatment may also be displayed. Between the treatment state 128 and the treatment suspension state 160, it is expressly contemplated that no other content, aside from one or more minor transition effects, is generated on the display interface 46. The content of the treatment suspension screen 162 is shown for exemplary purposes only, and any other information and graphics may be included.

Once the patient 13 has made the decision to return to sleep and continue treatment, the patient ventilation interface 12 is reconnected. When this occurs, it is possible for the controller 26 to detect the current breathing cycle position, and automatically activate the ventilation source 22. This is also referred to generally as a second modification to the pneumatic circuit that restores the same to a previous state before the first modification mentioned above. It is contemplated that detecting the re-activation of the ventilation source 22 is all that is needed to return the controller 26 to the treatment state 128 from the treatment suspension state 160. All of the other actions discussed above with respect to entering the treatment state 128 are performed, including the generating/updating of the patient interface fitment feedback indicator 118 and the treatment status screen 130. Alternatively, an affirmative input from the patient 13 selecting the treatment continuation user element 124 displayed in conjunction with the treatment suspension screen 162 may be part of the condition of returning to the treatment state 128.

Figure 11:
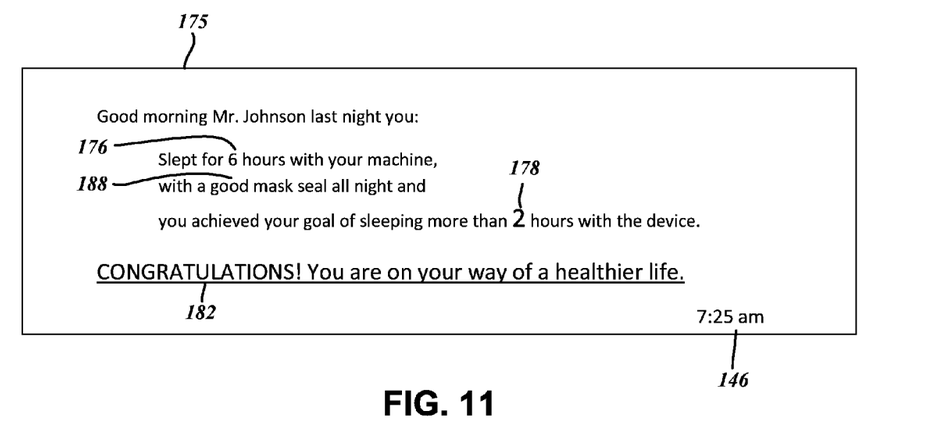
FIG. 11 is an example treatment conclusion screen.

If the treatment had concluded, i.e., the prescription pressure, accounting for the reduced pressure ramping period, was delivered to the patient for a duration set in the treatment duration time setting 122c, the controller 26 can transition to an alternative ventilation deactivation state 174. This is understood to be similar to the treatment suspension state 160 where the ventilation source 22 is turned off, but does not include the treatment continuation user element 172. Instead, as shown in the example of FIG. 11, a treatment conclusion screen 175 is generated. There is a different status message 164 that indicates the total sleep duration time 176, along with a total treatment duration time 178. Furthermore, the average patient ventilation interface fitment status 188 can be displayed. Another motivational message 182 can be displayed that corresponds to the specific treatment statistics, that is, whether or not the treatment duration goal was reached, and if not, then by how much it was missed, the patient ventilation interface fitment status throughout treatment, and so forth. The motivation message 182 can be modified based upon other usage statistics not specifically mentioned herein, but can be recorded by the controller 26.

In the illustrated example, because the patient 13 maintained good ventilation interface fitment and reached the set goal of two hours of treatment, the motivational message 182 is congratulatory in nature, further encouraging use. If any of these results were negative, however, a different motivation message that addresses any shortcomings in a positive manner ("You are almost there! Keep on going!") can be generated. Those having ordinary skill in the art will recognize many different possibilities for the motivational message. Again, like entering the treatment suspension state 160, when transitioning from the treatment state 128 to the ventilation deactivation state 174, no other content besides the treatment conclusion screen 175 and ancillary transition effects may be generated on the display interface 46. The content of the treatment conclusion screen 175, however, is presented by way of example only and not of limitation; other information and graphics may be included without departing from the scope of the present disclosure.

The particulars shown herein are by way of example and for purposes of illustrative discussion of the embodiments of the present disclosure only and are presented in the cause of providing what is believed to be the most useful and readily understood description of the principles and conceptual aspects. In this regard, no attempt is made to show details of the present invention with more particularity than is necessary, the description taken with the drawings making apparent to those skilled in the art how the several forms of the present invention may be embodied in practice.

What is claimed is:

1. A patient ventilation system comprising:
   a patient ventilation interface;
   a ventilator device adapted to be pneumatically coupled to a patient over the patient ventilation interface;
   a controller regulating airflow delivery from the ventilator device to the patient according to one or more predefined treatment configuration settings and having an inactive ventilation state entered upon powering on the patient ventilation system, a ventilation initiation state, a treatment state, a treatment suspension state, and a ventilation deactivation state;
   an input interface coupled to the controller; and
   a display interface coupled to the controller and configured to generate i) exclusively a device activation user element with the controller in the inactive ventilation state, ii) exclusively a patient ventilation interface fitment feedback indicator and a treatment screen with the controller in the ventilation initiation state, iii) exclusively the patient ventilation interface fitment feedback indicator and a treatment status screen with the controller in the treatment state concurrently with the ventilator device delivering the airflow to the patient over a predefined ramp characterized by a ramp pressure and a ramp time according to the treatment configuration settings defined from the treatment screen, iv) exclusively a treatment suspension screen with the controller in the treatment suspension state and the controller suspending the gas flow to the patient, and v) exclusively a treatment conclusion screen with the controller in the ventilation deactivation state and the controller stopping the ventilator device from delivering gas flow to the patient.

2. The system of claim 1, wherein the controller transitions from the inactive ventilation state to the ventilation initiation state in response to one of a user input detected on the input interface corresponding to a selection of the device activation user element and a detected activation of the ventilator device.

3. The system of claim 2, wherein the device activation user element is displayed substantially dominantly on the display interface.

4. The system of claim 1, wherein the treatment screen includes one or more modifiable user interface elements each showing predefined values and corresponding to the one or more treatment configuration settings.

5. The system of claim 4, wherein the one or more treatment configuration settings is a ramp pressure setting.

6. The system of claim 4, wherein the one or more treatment configuration settings is a ramp time setting.

7. The system of claim 4, wherein the one or more treatment configuration settings is a treatment duration time.

8. The system of claim 1, wherein the controller transitions from the ventilation initiation state to the treatment state in response to one of an input received on the input interface corresponding to a selection of a treatment continuation user element and an expiration of a time out period.

9. The system of claim 1, wherein the treatment conclusion screen includes a set of usage statistics data and a preselected patient motivational message corresponding to specific values of the set of usage statistics data.

10. The system of claim 9, wherein the set of usage statistics data includes a total usage duration.

11. The system of claim 9, wherein the set of usage statistics data includes a ventilation source activation duration.

12. The system of claim 9, wherein the set of usage statistics data includes a patient ventilation interface fitment feedback indicator average.

13. The system of claim 1, wherein the controller transitions from the treatment state to the ventilation deactivation state in response to at least one of an input received on the input interface corresponding to a selection of the treatment termination user element and a deactivation of the ventilator device.

14. The system of claim 1, wherein the input interface is a touch screen overlaid on the display interface, input received on the input interface spatially corresponding to a display position of the device activation user element.

15. The system of claim 1, wherein the device activation user element is rendered prominently over any other elements simultaneously displayed on the display interface.

16. The system of claim 1 wherein the device activation user element is the sole element displayed on the display interface at a given instance.

17. The system of claim 1, wherein the patient ventilation interface fitment feedback indicator includes a suggested corrective adjustment.

18. The system of claim 1, wherein the treatment status screen includes a clock display.

19. The system of claim 1, wherein the treatment status screen includes an elapsed time display.

20. The system of claim 19, wherein the elapsed time display is a countdown timer.

21. The system of claim 1, wherein the treatment status screen includes a ventilation delivery pressure indicator.

22. The system of claim 1, wherein the treatment status screen includes a ramping countdown timer display.

23. The system of claim 1, wherein the controller transitions from the treatment state to the treatment suspension state in response to a detection of either one or both of an input received on the input interface corresponding to a selection of a treatment suspension user element or a modification to a pneumatic circuit between the patient and the ventilator device.

24. The system of claim 23, wherein the first modification to the pneumatic circuit between the patient and the ventilator device is a disconnection of the patient ventilation interface from the patient.

25. The system of claim 23, wherein the first modification to the pneumatic circuit between the patient and the ventilator device is an introduction of an occlusion in the pneumatic circuit.

26. The system of claim 1, wherein the patient ventilation interface fitment feedback indicator includes a graphical illustration indicative of the fit of the patient ventilation interface.

27. A patient ventilation system comprising:
a patient ventilation interface;
a ventilator device adapted to be pneumatically coupled to a patient over the patient ventilation interface;
a controller regulating airflow delivery from the ventilator device to the patient and having an inactive ventilation state, entered upon powering on the patient ventilation system, in which airflow delivery is not yet initiated, a ventilation initiation state in which the controller initiates airflow delivery in accordance with preset values of one or more treatment configuration settings, a treatment state in which the controller continues airflow delivery in accordance with the one or more treatment configuration settings, a treatment suspension state in which the controller pauses the airflow delivery, and a ventilation deactivation state in which the airflow delivery is concluded;
an input interface coupled to the controller; and
a display interface coupled to the controller and configured to generate i) exclusively a device activation user element with the controller in the inactive ventilation state, ii) exclusively a patient ventilation interface fitment feedback indicator and a treatment screen with the controller in the ventilation initiation state, iii) exclusively the patient ventilation interface fitment feedback indicator and a treatment status screen with the controller in the treatment state concurrently with the ventilator device delivering the airflow to the patient over a predefined ramp characterized by a ramp pressure and a ramp time according to the treatment configuration settings defined from the treatment screen, iv) exclusively a treatment suspension screen with the controller in the treatment suspension state, and v) exclusively a treatment conclusion screen with the controller in the ventilation deactivation state.

* * * * *